United States Patent [19]

Collins et al.

[11] Patent Number: 4,578,505

[45] Date of Patent: Mar. 25, 1986

[54] ALLENIC PROSTANOIC ACID DERIVATIVES

[75] Inventors: Paul W. Collins, Deerfield; Richard M. Weier, Lake Bluff, both of Ill.

[73] Assignee: G. D. Searle & Co., Skokie, Ill.

[21] Appl. No.: 647,090

[22] Filed: Sep. 4, 1984

[51] Int. Cl.$^4$ .......................................... C07C 177/00
[52] U.S. Cl. ..................... 560/118; 560/53; 560/121; 562/463; 562/500; 562/503
[58] Field of Search ............... 560/121, 118, 53; 502/503, 500, 463

[56] References Cited

U.S. PATENT DOCUMENTS 3,879,438  4/1975  Crabbe et al. ............... 260/468
4,312,994  1/1982  Collins ........................ 560/121

Primary Examiner—Robert Gerstl
Attorney, Agent, or Firm—Steven M. Odre; Stuart L. Melton

[57] ABSTRACT

This invention relates to novel allenic prostanoic acid derivatives having the following formula

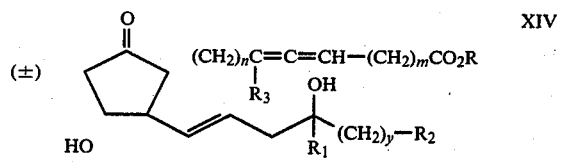

wherein R is hydrogen; or straight or branched chain alkyl of 1 to 6 carbon atoms, inclusive wherein $R_1$ is hydrogen; or straight or branched chain alkyl of 1 to 6 carbon atoms, inclusive; or vinyl ($-CH=CH_2$)

wherein $R_2$ is straight or branched chain alkyl of 1 to 6 carbon atoms; or cycloalkyl group containing 3 to 6 carbon atoms; or phenyl; or phenoxy wherein $R_3$ is hydrogen; or straight chain alkyl of 1 to 3 carbon atoms wherein m is an integer of from 1 to 4, inclusive, wherein n is an integer of from 1 to 3, inclusive with the proviso that the sum of m and n does not exceed 5, wherein y is an integer of from 1 to 3.

These compounds are useful by reason of their gastric antisecretory and cytoprotective activity.

12 Claims, No Drawings

ALLENIC PROSTANOIC ACID DERIVATIVES

BACKGROUND OF INVENTION

The present invention relates to certain novel organic compounds. In particular this invention relates to allene prostanoic acid derivatives of formula XIV.

The novel compounds of the present invention display valuable pharmacological properties as is exemplified by their ability to inhibit the gastric secretion stimulated by secretogogues such as histamine and pentagastrin. In addition, these compounds possess the remarkable ability to protect the gastric and intestinal mucosa against the damaging effects of such agents as ethanol and aspirin. This effect has been termed "cytoprotection" (see A. Robert et al., *Gastroenterology*, 77, 433 (1979)). Furthermore, these compounds have the surprising advantage of substantially decreased undesirable side effects such as diarrhea and uterine stimulant activity displayed by related substances. The gastric antisecretory activity is determined by standard laboratory means.

Gastric antisecretory agents may be used to treat such diseases as hypersecretion of gastric acid and peptic ulcer. A number of methods to control these conditions exist including, gastric antacids, antimuscarinic drugs, $H_2$-receptor blockers and prostaglandins (PG). Goodman and Gilman, Sixth Ed., 1980, pgs. 997, 632, 995–997 and 678.

PG analogs are all known to cause side effects, notably diarrhea. However, the capacity to suppress gastric secretion by these compounds is well documented.

PRIOR ART

Derwent 40258V/22 corresponding to U.S. Pat. No. 3,879,438 discloses prostaglandin dehydro analogs of $PGE_2$ and $PGF_{2\alpha}$ series possessing diethylenic unsaturation in the carboxylic acid chain which may be further substituted at C-4, C-6, and/or C-15 by a methyl, ethyl or propyl group. These compounds exhibit prostaglandin-type activity; i.e., bronchodilators, antihypertensives, CNS-depressants, menstruation controlling or abortion or labour-inducing agents.

SUMMARY OF THE INVENTION

The present invention provides a compound according to formula

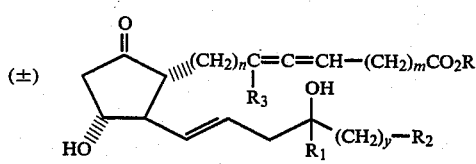

wherein R is hydrogen; or straight or branched chain alkyl of 1 to 6 carbon atoms, inclusive
wherein $R_1$ is hydrogen; or straight or branched chain alkyl of 1 to 6 carbon atoms, inclusive; or vinyl ($-CH=CH_2$)
wherein $R_2$ is straight or branched chain alkyl of 1 to 6 carbon atoms; or cycloalkyl group containing 3 to 6 carbon atoms; or phenyl; or phenoxy
wherein $R_3$ is hydrogen; or straight chain alkyl of 1 to 3 carbon atoms
wherein m is an integer of from 1 to 4, inclusive,
wherein n is an integer of from 1 to 3, inclusive with the proviso that the sum of m and n does not exceed 5,
wherein y is an integer of from 1 to 3.

The (±) refers to the compound shown, its mirror image and the mixture of racemates. Also included in the invention are the individual stereoisomers, and the mixture of isomers, wherein an alpha and beta isomer mixture is represented by the wavy lines in the above formula.

Further, alpha configurations are represented by a dashed line, and beta configurations are represented by a thick line, in the above formula.

The alkyl radicals represented in the foregoing structural formula are typified by methyl, ethyl, propyl, butyl, pentyl, and heptyl and the branched-chain radicals thereof.

The cycloalkyl groups represented in the foregoing structural formula are typified by cyclopropyl, cyclobutyl and cyclopentyl.

The specific assays used to detect gastric antisecretory activity are described as follows:

Heidenhain Pouch Dog Model

Adult female beagle dogs weighing 13–20 kg are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1N sodium hydroxide to pH 7.0. Following a 30 minute basal secretion the dogs are infused with a saline solution of histamine dihydrochloride at a dose of 1.0 mg/hr. The volume of the infusion is kept at approximately 13 ml/hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

Gastric Fistula Dog Model

Adult female beagle dogs weighing 6–11 kg. are prepared with whole stomach simple Thomas-type gastric cannulas.

Following full recovery from the surgical implantation of the gastric cannula, the dogs are trained to stand quietly, though fully conscious, in Pavlov-type dog restraining slings and are accustomed to intravenous histamine infusion.

Experiments are initiated by depriving dogs of food, but not water, for 18 hours. With an initial infusion of 0.15M sodium chloride, at a constant rate of 6.5 ml/hr, gastric secretions collected in plastic bottles affixed to the cannula, are taken at 15 minute intervals and measured for volume to the nearest 0.1 ml. Following a 30–45 minute basal secretion period, the collection bottles are removed, dosing plugs inserted, and compound administered. A 3.0 ml saline wash follows immediately.

After the end of a 30 minute drug absorption period the stomachs are emptied, collection bottles again attached, and the collections resumed at 30 minute intervals. Simultaneously, the saline infusion is replaced with a continuous intravenous infusion of histamine dihydrochloride in saline at 15 ug/kg/hr for four hours. Gastric samples are analysed for pH and titratable acidity determinations.

An analysis of the data for each measured or derived variable compares observations recorded following treatment with variables obtained for the same group of animals receiving histamine stimulation alone. Three parameters, gastric juice volume (ml/30 min), acid concentration (mEq/L), and total acid output (mEq/30 min) are analyzed individually. The data thus obtained are analyzed using interval-by-interval paired Student's t-test or two-way analysis of variance to achieve an indication of potency and duration of action. Percentage inhibition is calculated using pooled mean values for the four hour treatment period. Duration of activity is defined as the length of time of significant inhibition.

Meal Stimulated Pavlov-pouch Beagles

To evaluate the gastric antisecretory activity of these prostaglandins, each compound was administered either orally, intravenously or directly into the gastric pouch of surgically-prepared, meal-stimulated Pavlov pouch beagles. A neat solution of each agent was prepared from a stock ethanol solution immediately prior to dosing and was administered in a vehicle of 20% ethanol and 80% phosphate buffer.

Adult female beagles, 6-11 kg body weight, obtained from either Laboratory Research Enterprises (Kalamazoo, MI) or Hazelton Research Animals (Cumberland, VA) were surgically prepared by implanting a Thomas-type gastric cannula into an innervated (Pavlov) gastric pouch. In all studies gastric secretions were collected from the innervated pouches by gravity drainage. Following recovery each dog was trained to stand quietly in a dog restraining sling and ingest 10-12 ounces of either all beef dog food or cooked ground beef. In the course of these studies, no dog was used more than once a week.

Dogs were deprived of food, but not water, for 24 hours prior to experimentation. Following a 30 minute basal secretion period, the test agent was administered either orally in gelatin capsules, intravenously or directly into the gastric pouch. At the end of an additional 30 minute period to allow for drug absorption, the gastric pouch was emptied of its contents. At this point gastric secretory stimulation was achieved by feeding. The volume (ml/30 min) and titratable acidity (mEq/L) were measured and total acid output (mEq/30 min) was calculated for gastric secretions collected over 30 minute intervals for 240 minutes after compound administration.

The analysis of data was based upon a comparison of treated vs. control experiments. Percentage inhibition for the four hour period was calculated for individual dogs but is expressed as the mean value for those dogs of the control and treated group.

The specific assay used to detect cytoprotective activity is described as follows:

Male, Charles River rats, weighing 180 to 220 g, which are food deprived for 24 hours are administered a test compound. Thirty minutes later, each rat is given 1.0 ml of absolute ethanol intragastrically. The rats are sacrificed sixty minutes after alcohol administration and gastric mucosae are visually examined for the presence of lesions. Objective scoring is based on the presence or absence of lesions and data recorded as the number of rats per group completely protected from lesion formation.

Diarrhea is an undesirable side effect commonly associated with antisecretory and cytoprotective prostaglandins. Diarrheogenic activity is demonstrated by the following standardized test.

Groups of six adult male Charles River rats, weight range 180 to 200 grams, are fasted for 24 hours prior to administering the test substance. The prostaglandin to be tested is administered intragastrically in iso-osmotic phosphate buffer at a volume of 10 ml/kg at doses ranging from 100 to 3000 microgram/kg. Control animals receive only the vehicle. The rats are placed in individual wire mesh cages and the trays lined with brown paper. Diarrhea is assessed at hourly intervals on an all or none basis for up to eight hours after administration of the prostaglandin. Diarrhea is defined as any loose or watery stool. $ED_{50}$ values are assessed for each hourly diarrheogenic response.

Compounds of this invention were tested as above and found to be antisecretory and cytoprotective. By virtue of these activities, the compounds of the invention are useful in treating and alleviating gastric ulcers in mammals.

The compounds of the present invention are formulated into pharmaceutically acceptable dosage forms by conventional methods known to the pharmaceutical art. For example, the compounds can be administered in oral unit dosage forms such as tablets, capsules, pills, powders, or granules. They also may be administered rectally or vaginally in such forms as suppositories or bougies; they may also be introduced in the form of eye drops, intraperitoneally, subcutaneously, or intramuscularly, using forms known to the pharmaceutical art. In general the preferred form of administration is oral.

An effective but non-toxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 0.25 $\mu$g/kg up to at least 50 $\mu$g/kg orally. When other forms of administration are employed equivalent doses are administered.

The compounds of this invention are prepared by the general methods illustrated in the accompanying Charts A, B and C. Chart A: Furfural, Formula I, reacts with omega-alkynyl magnesium halides, II, Grignard reagents prepared by methods known to those skilled in the art from omega-haloalk-1-ynes, to form the intermediate compounds of Formula III. Where n is greater than 1, the acetylene group of the Grignard is protected by a trialkylsilyl group that can later readily be removed by treatment with potassium fluoride. Where n is 1, R may be hydrogen and no deprotection is necessary to yield compound III. Preferred reaction conditions include addition at ca. 0° of a tetrahydrofuran solution of compound I to a diethyl ether solution of the freshly prepared Grignard reagent. Compounds III are typically purified by distillation at reduced pressure. The intermediates III rearrange upon heating under acidic conditions to form cyclopentenyl compounds of Formula IV. Preferred conditions include heating at ca. 80°–85° in aqueous dioxane containing p-toluenesulfonic acid. Crude compounds IV are typically purified by extraction and column chromatography on silica gel. Compound IV further rearranges under acidic or basic conditions to form the isomeric compounds of Formula V. Preferred conditions include treatment of compounds IV with basic Grade III alumina at room temperature.

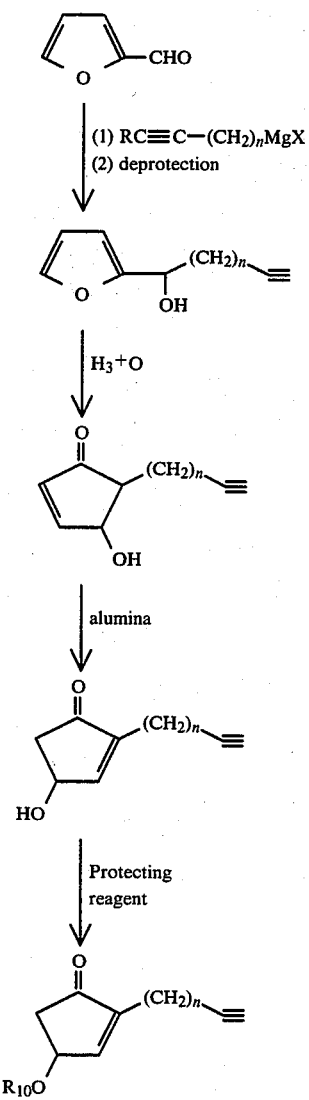

CHART A

Protection of alcohol intermediates V, using a protecting group ($R_{10}$) such as trialkylsilyl or tetrahydropyranyl, by reaction in an inert organic solvent affords the protected derivatives, Formula VI. Preferred reagents and conditions include triethylsilyl chloride and imidazole in dimethylformamide at room temperature. The intermediate compounds VI are typically purified by column chromatography on silica gel.

Chart B: Compounds VI react first with organocopper reagents, Formula VII (prepared by the general method described in U.S. Pat. No. 4,271,314) and then with suitable silylating reagent to form intermediates of Formula VIII. Preferred conditions include reaction of VI and VII at ca. −60° in diethyl ether, followed by addition of a trialkylsilyl chloride, preferably with at least one bulky alkyl group (e.g. t-butyldimethylsilyl chloride) which will increase yields and stability, and hexamethylphosphoric triamide, with warming to ca. −20°. After extracting into an organic solvent, such as diethyl ether, and stripping volatiles, the crude intermediates VIII are typically purified by column chromatography on silica gel. The acetylenic intermediates VIII, are reacted with strong non-aqueous base in an inert organic solvent solution and the appropriate ester aldehyde to provide the intermediate of formula IX.

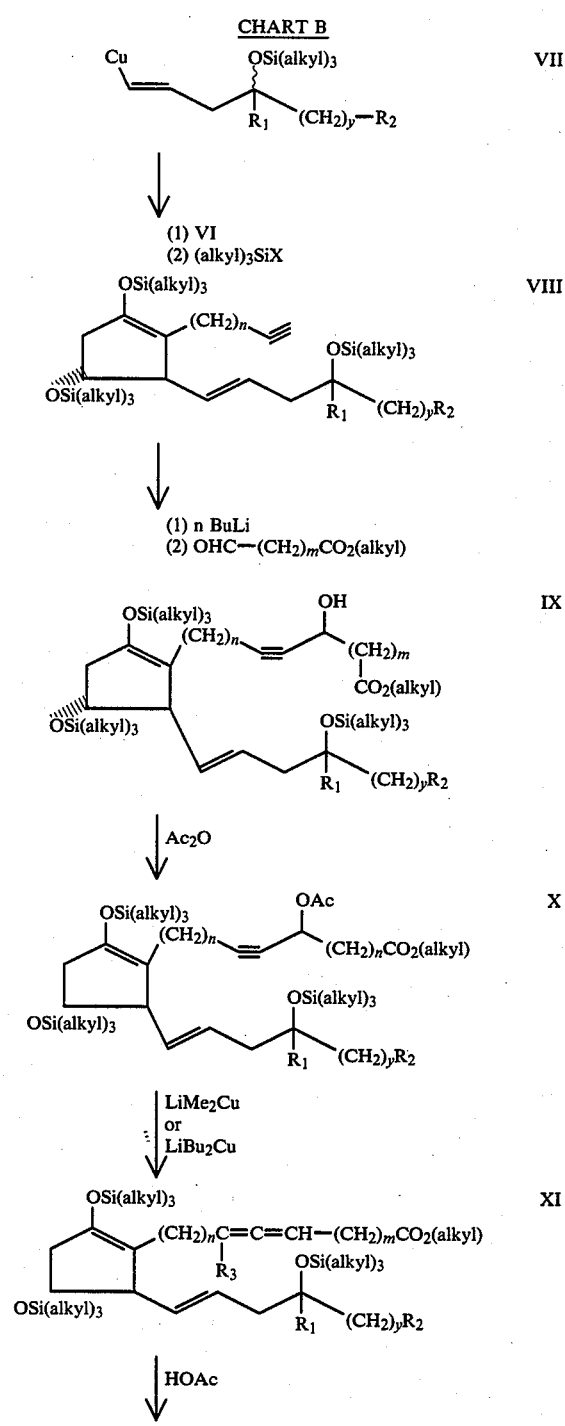

CHART B

-continued
CHART B

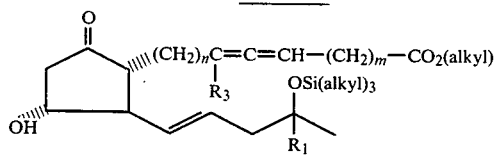
XII

Preferred reaction condition include reaction of VIII with n-butyllithium in tetrahydrofuran at ca −30°, followed by the addition of the ester aldehyde at −60° in tetrahydrofuran. Intermediates IX are typically purified by column chromatography on silica gel. Treatment of the intermediates of formula IX with an acylating agent provides the intermediates of formula X. Preferred conditions include the reaction of the intermediates of formula IX in pyridine at 0° with acetic anhydride. Intermediates of formula X are purified by column chromatography on silica gel. Treatment of the intermediates of formula X with lithium dibutylcuprate or lithium dimethylcuprate provides the intermediates of formula XI. Preferred conditions include the reaction of the intermediates of formula X in ethyl ether at ca. −70 with lithium dibutyl cuprate which was prepared by the reaction of n-butyl lithium at −40° with copper (1) iodide in ethyl ether. Hydrolysis of the protected compounds of XI under acidic conditions affords the compounds of Formula XII. Preferred hydrolytic conditions include a 3:1:1 mixture of acetic acid/tetrahydrofuran/water stirred at room temperature. Compounds are typically purified by column chromatography on silica gel.

Chart C: An alternative method for the preparation of compounds of formula XII and the preferred method for the compound of formula XII wherein $R_1$ methyl, $R_2$ propyl, $R_3$ is hydrogen, m is 3, n is 1 and y is 1 is illustrated in Chart C.

CHART C

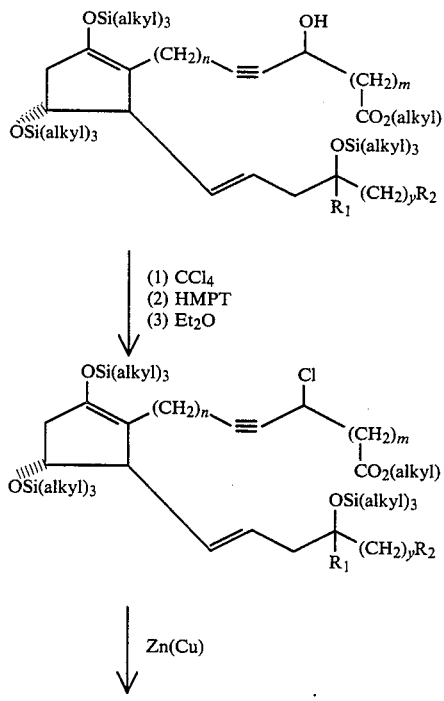

-continued
CHART C

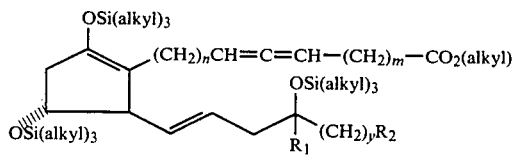
XI

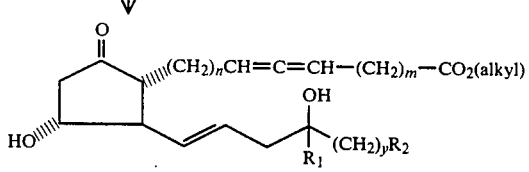
XII

Compounds of formula IX in diethyl ether are treated with carbon tetrachloride and hexamethylphosphorous triamide. Preferred conditions include the reaction of the compounds of formula IX and carbon tetrachloride in diethyl ether under a nitrogen atmosphere with stirring, followed by the addition of hexamethylphosphorous triamide. After extracting into an organic solvent and stripping volatiles, the crude intermediates of formula XIII are purified by column chromatography on silica gel. The intermediates of formula XIII are then reacted with Zn(Cu). Preferred conditions include the reaction of the compounds of formula XIII with Zn(Cu) in ethanol containing glacial acetic acid with stirring. After extracting into an organic solvent and stripping volatiles the crude intermediates of formula XI are purified by column chromatography on silica gel.

The deprotection of the compounds of formula XI was accomplished by treatment with a mixture of acetic acid/tetrahydrofuran/water stirred at room temperature. Compounds of formula XII are purified by column chromatography on silica gel.

The preparation of the compounds of formula XIV wherein R is hydrogen is described in U.S. Pat. No. 4,271,314.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions or processes of the following preparative procedures can be used to prepare these compounds. All temperatures are degree Celsius unless otherwise noted.

DESCRIPTION OF THE PREPARATION OF STARTING MATERIALS

Example A

Preparation of α-(2-propynyl)-2-furanmethanol

Propargyl magnesium bromide was prepared by adding a solution of propargyl bromide (as 145.5 g of 80%, by weight, solution in toluene; 0.976 mole) in 150 ml of diethyl ether to a slurry of 26 g (1.07 mole) of iodine-activated magnesium and 340 mg of mercuric chloride in 450 ml of ether. The rate of addition was adjusted to maintain a vigorous reflux. After addition was complete, the reaction mixture was stirred at room temperature for one hour and then cooled to 0°. A solution of 75 g (0.78 mole) of 2-furancarboxaldehyde in 400 ml of tetrahydrofuran was added dropwise, and the reaction mixture was stirred at room temperature for fifteen minutes, then poured onto a cold saturated ammonium chloride solution and stirred vigorously. The layers were separated and the aqueous layer was extracted with ether. The organic phase was washed with saturated ammonium chloride solution and with brine, dried over sodium sulfate, filtered, and concentrated to dryness. Distillation of the crude material at 1.0 torr gave 100.6 g of the title compound, b.p. 68°–72°. Structure assignment was confirmed by the proton nmr spectrum: 2.05 (t, J=2–3 HZ, ≡C—H), 2.59 (d of d, J=2–3 and 5–6 Hz, —CH$_2$—C≡), 4.80 (q,.J=5–6 Hz, —CHOH—), 6.27 and 7.32 ppm (furan).

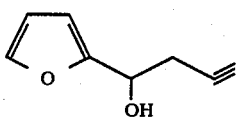

Example B 4-hydroxy-2-(2-propynyl)-2-cyclopenten-1-one

To a solution of 40.2 g (0.295 mole) of the title compound of Example 1 in 800 ml of a 8:1 dioxane/water mixture was added 4 g (0.021 mole) of p-toluenesulfonic acid monohydrate. The reaction mixture was heated at 83° for 36 hours under argon, cooled, and diluted with 500 ml of ethyl acetate. The organic phase was washed once with water and two times each with 5% sodium bicarbonate solution and brine solution. The aqueous washes were combined and extracted with ethyl acetate. The combined organic phases were dried over sodium sulfate, filtered, and concentrated. Chromatography of the combined crude materials on silica gel (using 25% ethyl acetate in hexane as eluent) gave 12.45 g of the intermediate compound 4-hydroxy-5-(2-propynyl)-2-cyclopenten-1-one as a viscous oil. Structure assignment was confirmed by the proton nmr spectrum.

A solution of 14.5 g (0.11 mole) of the cyclopentenone intermediate in 50 ml of ether was poured into a column packed with 282 g of Grade III alumina (6% water by weight). The column was closed and allowed to stand at room temperature for twenty four hours. The product was eluted from the column with mixtures of diethyl ether and ethyl acetate to give 7.3 g of the title compound as a viscous oil. Structure assignment was confirmed by the proton nmr spectrum:

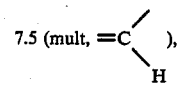

4.98 (—CHOH), 2.16 (t, J=2–3 Hz, ≡C—H), 3.07 ppm (mult, J=—CH$_2$—C≡).

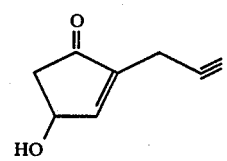

Example C 2-(2-propynyl)-4-[(triethylsilyl)oxy]-2-cyclopenten-1-one

A solution of 250 mg (1.84 mmole) of the title compound of Example B in 4 ml of dimethylformamide was treated successively with 200 mg (3 mmole) of imidazole and 300 mg (2 mmole) of triethylsilyl chloride. After stirring for thirty minutes, the reaction mixture was diluted with water, washed with diethyl ether, dried over sodium sulfate, filtered, and concentrated to dryness. The crude material was chromatographed on silica gel to give 0.37 g of the title compound as an oil. Structure assignment was confirmed by the proton nmr spectrum: 2.13 (t, J=2 Hz, ≡C—H), 3.08 (mult, —CH$_2$—C≡), 4.90 (mult C-11),

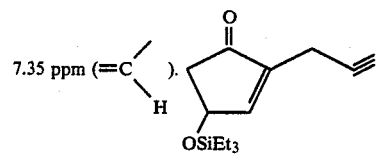

Example D (1,1-dimethylethyl)dimethyl[[3β-[4-methyl-4-[(trimethylsilyl)oxy]-1E-octenyl]-2-(2-propynyl)-4α-[(triethylsilyl)oxy]-1-cyclopenten-1-yl]oxy]silane A solution of 10 g (0.02 mole) trimethyl[1-methyl-1-[3-(tributylstannyl)-2E-propenyl]pentoxy]silane in 25 ml of tetrahydrofuran was cooled to −60° under an argon atmosphere, and 11.8 ml of a 1.7M solution of n-butyllithium in hexane (0.02 mole) was added. The reaction mixture was stirred for forty five minutes, after which a solution of 2.62 g (0.02 mole) of copper-1-pentyne and 6.4 g (0.04 mole) of hexamethylphosphorus triamide in 75 ml of ether was added dropwise. After ten minutes, a solution of 2.4 g (0.01 mole) of the title compound of Example 3 in 20 ml of ether was added, and the reaction mixture was stirred an additional 45 minutes. A solution of 3 g (0.02 mole) of t-butyldimethylsilyl chloride in 15 ml of ether was added, followed by the addition of 25 ml of hexamethylphosphoric triamide. The temperature was allowed to rise to −20°, where it was maintained for one hour. The reaction mixture was poured into 1N hydrochloric acid and ether. The layers were separated and the organic phase was washed with water, dried over sodium sulfate, filtered, and concentrated to dryness. The crude material was chromatographed on silica gel to give 4 g of the title compound as a viscous oil. Structure assignment was confirmed by the proton nmr spectrum: 1.80 (t, J=1–2 Hz, ≡C—H), 4.95–5.80 (mult, —CH=CH—), 0.90 ppm (t-Bu).

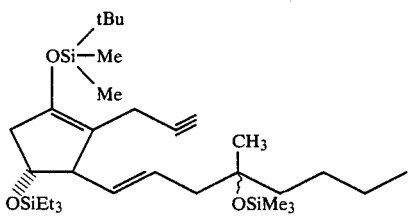

EXAMPLE 1

Preparation of methyl 4-hydroxy-9-[[(1,1-dimethylethyl)dimethylsily]oxy]-16-methyl-11α-[(triethylsilyl)oxy]-16-[(trimethylsilyl)oxy]-prosta-8,13E-dien-5-yn-1-oate To a stirred solution of 1.993 g (3.45 mmole) of (1,1,-dimethylethyl)dimethyl[[3β-[4-methyl-4-[(trimethylsily)oxy]-1E-octenyl]-2-(2-propynyl)-4α-[(triethylsily)oxy]-1-cyclopenten-1-yl]oxy]silane in 15 ml of anhydrous tetrahydrofuran cooled to −30° under a nitrogen atmosphere, using a trace of triphenyl methyl chloride as an indicator, was added, dropwise, 2.0 ml of 1.66M n-butyllithium in hexane until the red triphenyl methyl anion endpoint was achieved. After stirring for an additional five minutes, the reaction mixture was cooled to −70° at which time a solution of 1.20 g (10.3 mmole) of methyl 3-formyl propanoate in 2 ml of tetrahydrofuran was added. The resulting reaction mixture was stirred for 90 minutes at −70° before being poured into water. The resulting product was extracted into ether which was then washed with saturated aqueous sodium chloride, filtered, dried over anhydrous sodium sulfate, and concentrated to dryness. The resulting residue was purified by chromatography on a silica gel column, using mixtures of ethyl acetate and hexane as eluent. Removal of the solvent afforded the title compound having the following structural formula

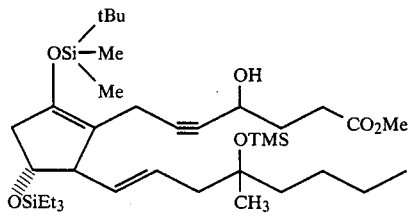

NMR: (CDCl3, ppm) 3.65 (Me), 4.00, (CHOH), 4.35,

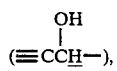

4.9-5.85 (—CH═CH—), 1.15 (—CH2—CH3).

EXAMPLE 2

Preparation of methyl 4-(acetyloxy)-9-[[(1,1-dimethylethyl)dimethylsily]oxy]-16-methyl-11α-[(triethylsilyl)oxy]-16-[(trimethylsilyl)oxy]prosta-8,13E-dien-5-yn-1-oate To a stirred, cold (0°) solution of 456 mg (0.66 mmol) of methyl 4-hydroxy-9-[[(1,1-dimethylethyl)dimethylsilyl]-oxy]-16-methyl-11α-[(triethylsilyl)oxy]-16-[(trimethylsilyl)oxy]prosta-8,13E-dien-5-yn-1-oate in 3 ml of pyridine was added 0.18 ml (1.90 mmol) of acetic anhydride. After 5 minutes the ice bath was removed, the reaction mixture was stirred at room temperature for 7 hours and then stored in the refrigerator overnight. The reaction mixture was stirred an additional 5 hours at room temperature before being poured into water and extracted with diethyl ether. The ether layer was backwashed with saturated aqueous sodium chloride solution, dried over sodium sulfate, filtered and concentrated to dryness. The resulting oily residue was purified by chromatography on a silica gel column, using ethyl acetate and hexane as the eluent. Removal of the solvent afforded the title compound having the following structure

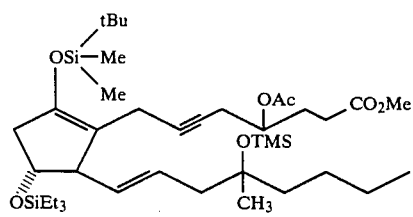

NMR: (CDCl3, ppm) 3.65 (MeO), 2.02 (COCH3).

EXAMPLE 3

Preparation of methyl 9-[[(1,1-dimethylethyl)dimethylsily]oxy]-16-methyl-11α-[(triethylsilyl)oxy]-16-[(trimethylsilyl)oxy]prosta-4,5,13E-trien-1-oate A reaction mixture containing lithium dibutylcuprate which was prepared by adding 1.54 ml of n-butyllithium solution in hexane (1.53M) to a stirred slurry of 225 mg (1.08 mmole) of cuprous iodide in 15 ml of ethyl ether under a nitrogen atmosphere at −40°, was stirred 25 minutes at this temperature. The reaction mixture was then cooled to −70° with stirring at which time 222 mg (0.3 mmole) of methyl 4-(acetyloxy)-9-[[(1,1-dimethylethyl)dimethylsily]oxy]-16-methyl-11α-[(triethylsilyl)oxy]-16-[(trimethylsilyl)oxy]prosta-8,13E-dien-5-yn-1-oate in 2 ml of ethyl ether was added. After 30 minutes of stirring the reaction mixture was poured onto 0.5N hydrochloric acid and extracted with ethyl ether. The ether layer was backwashed with brine, dried over sodium sulfate, filtered, and concentrated to dryness. Chromatography of the crude material on silica gel and using ethyl acetate/hexane as the eluent afforded as a colorless oil the title product having the following structure

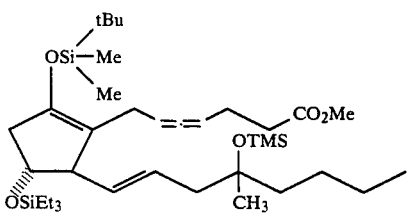

EXAMPLE 4

Preparation of methyl 11α,16-dihydroxy-16-methyl-9-oxoprosta-4,5,13E-trien-1-oate A mixture of 74 mg of methyl 9-[[(1,1-dimethylethyl)-dimethylsily]oxy]-16-methyl-11α-[(triethylsilyl)oxy]-

16-[(trimethylsilyl)oxy]prosta-4,5,13E-trien-1-oate in 5 ml of a 3:1:1 solution of acetic acid/tetrahydrofuran/water was stirred at room temperature for 24 hours. The reaction was then concentrated on the rotary evaporator, diluted with water and extracted three times with ethyl ether. The combined ether layers were washed twice with saturated aqueous sodium chloride solution, once with 5% aqueous sodium bicarbonate solution, twice again with saturated aqueous sodium chloride solution, dried over sodium sulfate, filtered and concentrated to dryness. The crude material was chromatographed on silica gel using ethyl acetate/hexane as the eluent to give the title compound having the following structure.

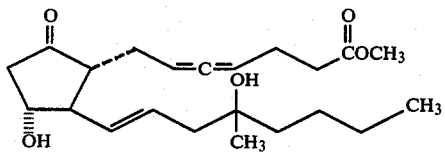

NMR: (CDCl₃, ppm) 3.65 (OCH₃), 5.05 (HC=C=CH), 4.05 (C-11) 5.50 (multiplet C-13,14).

EXAMPLE 5

Preparation of 5-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-2-pentynal The title compound was prepared by the method of Example 1 using 644 mg of (1,1-dimethylethyl)dimethyl[[3β-[4-methyl-4-[(trimethylsilyl)oxy]-1E-[octenyl]-2-(3-butynyl)-4α-[(triethylsilyl)oxy]-1-cyclopenten-1-yl]oxy]silane in 6 ml of tetrahydrofuran, 0.32 ml of 1.58M. n-butyllithium in hexane and 232 mg of dimethylformamide in 1 ml of tetrahydrofuran. Chromatography of the crude material on a silica gel column using ethylacetate/hexane as the eluent afforded the title product having the following structure

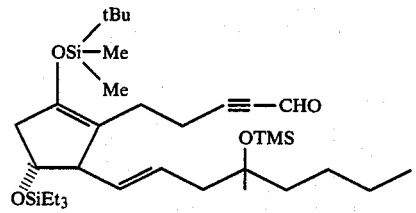

EXAMPLE 6

Preparation of methyl 3-hydroxy-7-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-4-heptnoate LDA was prepared by adding 1.1 ml of a 1.66M solution of n-butyllithium in hexane to a stirred solution of 191 mg of diisopropylamine (1.89 mmol) in 3 ml of tetrahydrofuran at −20° to −30° C. under a nitrogen atmosphere. The reaction mixture was cooled to −60° to −70° C. and a solution of 146 mg of methyl acetate (1.97 mmol) in 2 ml of tetrahydrofuran was added, dropwise. After stirring for 10 minutes 568 mg of 5-[2-[[1,1-dimethylethyl)-dimethyl-silyl]oxy]-5β-[4-methyl-4-[(trimethylsilyl)-oxy]-1E-octenyl]-4α-[(triethylsilyl)-oxy]-1-cyclopenten-1-yl]-2-pentynal in 6 ml of tetrahydrofuran was added, dropwise. The reaction mixture was stirred for 2 hours at −60° to −70° C., poured onto a saturated aqueous ammonium chloride solution and extracted three times with diethyl ether. The combined organic layers were washed three times with saturated aqueous sodium chloride solution, dried over sodium sulfate, filtered and stripped on the rotary evaporator to give the crude product as an oil. Chromatography of the crude product on a silica gel column using ethyl acetate/hexane as the eluent afforded the title compound having the following structure

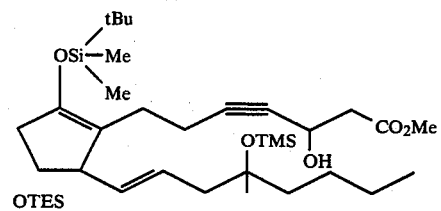

EXAMPLE 7

Preparation of methyl 3-(acetyloxy)-7-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-4-heptynoate The title compound was prepared by the method of Example 2 using 453 mg (0.65 mmol) of methyl 3-hydroxy-7-[2-[[(1,1-dimethyl-ethyl)dimethylsilyl]oxy]-5β-[4-methyl-4-[(trimethylsilyl)-oxy]-1E-octenyl]-4α-[(triethylsilyl)-oxy]-1-cyclopenten-1-yl]-4-heptynoate in 3 ml of pyridine and 0.15 ml of acetic anhydride. Chromatography of the crude material on silica gel column using 8% ethyl acetate/hexane as the eluent afforded the title compound having the following structure

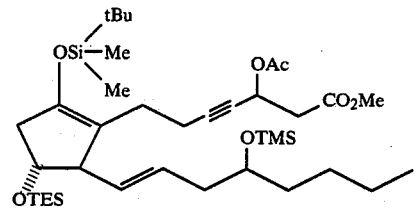

EXAMPLE 8

Preparation of methyl 9-[[(1,1-dimethylethyl)dimethylsilyl]oxy]-16-methyl-11α-[(triethylsilyl)oxy]-16-[(trimethylsilyl)oxy]prosta-3,4,8,13E-tetraen-1-oate The title compound was prepared by the method of Example 3 using lithium dimethyl cuprate (prepared from 2.8 ml of a 1.5M etheral solution of methyl lithium and 303 mg of cuprous iodide in ethyl ether at −20° to −30°) and 266 mg of (0.4 mmol) methyl 3-(acetyloxy)-7-[2-[[(1,1-dimethylethyl)-dimethylsilyl]oxy]-5β-[4-methyl-4-[(trimethylsilyl)oxy]-1E-octenyl]-4α-[(triethylsilyl)oxy]-1-cyclopenten-1-yl]-4-heptynoate.

Chromatography of the crude product on silica gel using 20% ethyl acetate/hexane as the eluent afforded the titled compound having the following formula

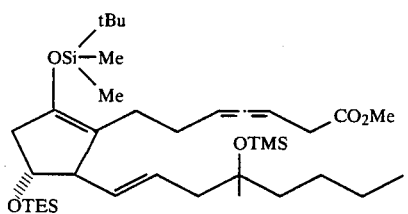

EXAMPLE 9

Preparation of methyl 11α,16-dihydroxy-16-methyl-9-oxoprosta-3,4,13E-trien-1-oate The title compound was prepared by the method of Example 4 using 83 mg of methyl 9-[[(1,1-dimethylethyl)dimethylsilyl]oxy]-16-methyl-11α-[(triethylsilyl)oxy[-16-[(trimethylsilyl)oxy]prosta-3,4,8,13E-tetraen-1-oate compound and 5 ml of a 3:1:1 solution of acetic acid/tetrahydrofuran/water. Chromatography of the crude material on silica gel using ethyl acetate/hexane combinations as the eluents afforded the titled compound, having the following structure

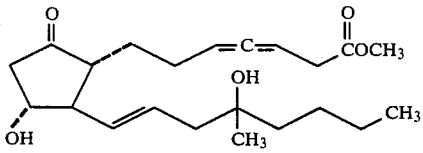

NMR: (CDCl3, ppm) 1.16 (C-16 CH3), 4.05 (C-11), 3.68 (OCH3).

EXAMPLE 10

Preparation of methyl 4-hydroxy-8-[2-]](1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-5-octynoate The title compound was prepared by the method of Example 1 using 565 mg of (1,1-dimethylethyl)dimethyl[[3β-[4-methyl-4-[(trimethylsilyl)oxy]-1-[octenyl]-2-(3-butynyl)-4α-[(triethylsilyl)oxy]-1-cyclopenten-1-yl]]oxy]silane in 7 ml of tetrahydrofuran, 0.69 ml of 1.66M n-butyllithium in hexane, and 331 mg of OHC(CH2)2CO2Me in 1 ml of tetrahydrofuran. Chromotagraphy of the crude material on a silica gel column using ethyl acetate/hexane mixture as the eluent afforded the title compound having the following structure

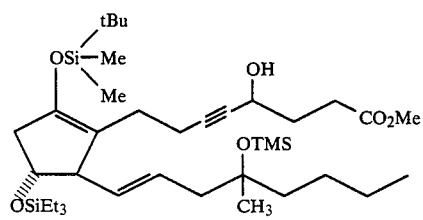

NMR: (CDCl3, ppm): 4.40 (—CHOH—); 3.90 (—CHOSiEt3—); 3.65 (OMe); 1.15 (—CCH3(OTMS)—); complex multiplet centered; about 5.3 ppm (trans vinyl protons).

EXAMPLE 11

Preparation of methyl 4-(acetyloxy)-8-[2-[[(1,1-dimethylethyl)dimethylsilyl]oxy]-5β[4-methyl-4-[(trimethylsilyl)oxy]-1E-octenyl]-4α-[(triethylsilyl)oxy]-1-cyclopenten-1-yl]-5-octynoate The title compound was prepared by the method of Example 2 using 546 mg of methyl 4-hydroxy-8[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-5-octynoate in 7 ml of pyridine and 0.35 ml of acetic anhydride. Chromatography of the crude product on a silica gel column using 7% ethyl acetate/hexane as the eluent afforded the title compound having the following structure

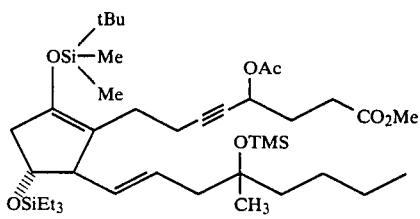

NMR: (CDCl3, ppm): 2.05 (CH3CO); 3.65 (OMe).

EXAMPLE 12

Preparation of methyl 8-[2-[[(1,1-dimethylethyl)dimethylsilyl]oxy]-5β[4-methyl-4-[(trimethylsilyl)oxy]-1E-octenyl]-4α-[(triethylsilyl)oxy]-1-cyclopenten-1-yl]-4,5-octadienoate The title compound was prepared by the method of Examples 3 and 8 using 5.0 ml of a 1.5M etheral solution of methyl lithium, 453 mg of cuprous iodide in ethyl ether and 448 mg (0.59 mmol) of methyl 4-(acetyloxy)-8-[2-[[(1,1-dimethylethyl)dimethylsilyl]oxy]-5β[4-methyl-4-[(trimethylsilyl]oxy]-1E-octenyl]-4α-[(triethylsilyl)oxy]-1-cyclopenten-1-yl]-5-octynoate.

Chromatography of the crude material on silica gel column using 3% ethyl acetate/hexane as the eluent afforded the title compound having the following structure

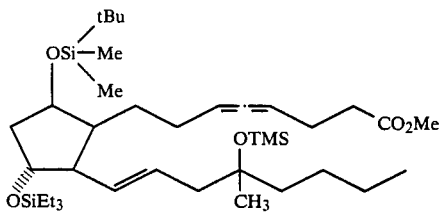

EXAMPLE 13

Preparation of methyl 8-[3α-hydroxy-2β(4-hydroxy-4-methyl-1E-octenyl)-5-oxo-1α-cyclopentyl]-4,5-octadienoate The title compound was prepared by the method of Example 4 using 371 mg of methyl 8-[2-[[1,1-dimethylethyl)dimethylsilyl]oxy]-5β-[4-methyl-4-[(trimethylsily)oxy]-1E-octenyl]-4α-[(triethylsilyl)oxy]-1-cyclopenten-1-yl]-4,5-octandienoate and 20 ml of a 3:1:1 solution of acetic acid/tetrahydrofuran/water. Chromatography of the crude material on silica gel using 80% ethyl acetate/hexane as the eluent afforded the title compound having the following structure

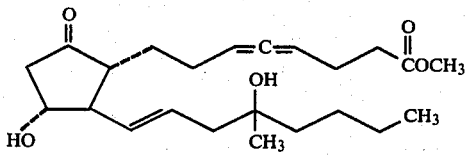

NMR: (CDCl₃, ppm): 5.10 (allene H); 4.05 (—CH(OH—); 3.65 (OMe).

EXAMPLE 14

Preparation of methyl 5-hyroxy-8-[2-[[(1,1-dimethylethyl)dimethylsilyl]oxy]-5β-[4-methyl-4-[(trimethylsilyl)oxy]-1-E-octenyl]-4α-[(triethylsilyl)oxy]-1-cyclopenten-1-yl]-6-octynoate The title compound was prepared by the method of Example 1 using 658 mg of (1,1-dimethylethyl)dimethyl[[3β-[4-methyl-4-[(trimethylsilyl)oxy]-1-[octenyl]-2-(2-propynyl)-4α-[(triethylsilyl)oxy]-1-cyclopenten-1-yl]oxy]silane in 8 ml of tetrahydrofuran, using 0.89 ml of 1.53M n-butyllithium in hexane, and 443 mg of OHC(CH₂)₃CO₂Me in 2 ml of tetrahydrofuran. Chromatography of the crude material on a silica gel column using 20% ethyl acetate/hexane as the eluent afforded the title compound having the following structure

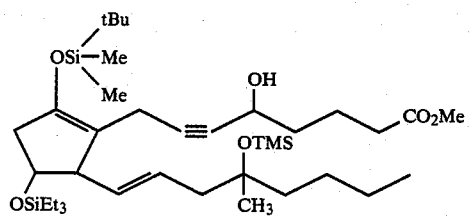

EXAMPLE 15

Preparation of methyl 5-chloro-8-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-6-octynoate A solution of methyl 5-hydroxy-8-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-6-octynoate (258 mg, 0.36 mmol) and carbon tetrachloride (278 mg, 1.80 mmol) in anhydrous ethyl ether (12 ml) was stirred at 0° under nitrogen. To this solution was added hexamethylphosphorous triamide (182 mg, 1.12 mmol) in anhydrous ethyl ether (3 ml). The reaction was stirred for 2 hours at 0°.

The reaction was poured onto saturated aqueous sodium chloride solution and extracted four times with diethyl ether. The combined ether layers were backwashed three times with saturated aqueous sodium chloride solution and dried over sodium sulfate. Filtration of the drying agent and stripping the filtrate gave 282 mg of brown oil. This oil was chromatographed on silica using 2% ethyl acetate/hexane as the eluent to give 221 mg of the pure chloride, title compound having the following structure

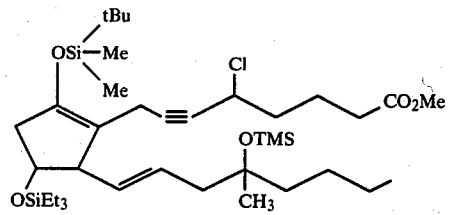

EXAMPLE 16

Preparation of methyl 8-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-5,6-octadienoate To a solution of methyl 5-chloro-8-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-6-octynoate (213 mg, 0.29 mmol) in absolute ethanol (10 ml) stirred at room temperature was added approximately 100 mg of zinc copper couple and glacial acetic acid (0.05 ml). After stirring for 30 min. more zinc copper couple was added, bringing the total employed in this reaction to 212 mg. After stirring another 30 min. tlc showed reaction to be complete.

The reaction was filtered and stripped. The residue was extracted thoroughly with hexane by decantation and the extract stripped in vacuo to give 181 mg of a colorless oil. This material was chromatographed on silica using 100% hexane, 0.5% and 1% ethyl acetate/hexane as eluents to give 144 mg of the title compound having the following structure

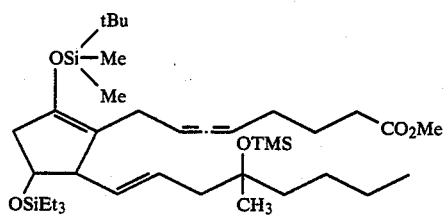

NMR: (CDCl₃, ppm) 3.95 (mult., —CH(OSiEt₃)—); 3.65 (OCH₃); 4.98 (mult., allene protons); 5.35 (mult, trans vinyl protons).

EXAMPLE 17

Preparation of methyl 8-[3α-hydroxy-2β-(4-hydroxy-4-methyl-1E-octenyl)-5oxo-1α-cyclopentyl]-5,6-octadienoate The title compound was prepared by the method of Example 4 using 160 mg of methyl 8-[2-[[(1,1-dimethylethyl)dimethylsilyl]oxy]-5β-[4-methyl-4-[(trimethylsilyl)oxy]-1E-octenyl]-4α-[(triethylsilyl)oxy]-1-cyclopenten-1-yl]-5,6-octodienoate in 10 ml of a 3:1:1 solution of acetic acid/tetrahydrofuran/water. Chromatography of the crude product on silica using 50% ethyl acetate/hexane as eluent afforded the title compound having the following structure:

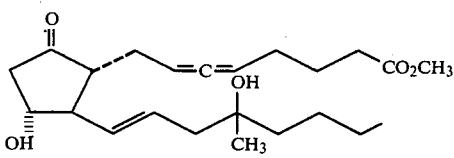

NMR: (CDCl₃, ppm) 5.05 (mult., allene H); 4.08 (mult., —CH(OH)—); 3.65 (OCH₃); 5.6 (mult., trans vinyl H).

EXAMPLE 18

Preparation of methyl 11α,16-dihydroxy-6,16-dimethyl-9-oxoprosta-4,5 13E-trien-1-oate Lithium dimethyl cuprate was prepared at −20° to −30° under an argon atmosphere by adding 3 ml of a 1.5M solution of methyl lithium in diethyl ether to a stirred slurry of 328 mg of cuprous iodide in 6 ml of diethyl ether until the characteristic color of MeCu was gone. After addition was complete the reaction mixture was stirred at −20° to −30° for ten minutes and then cooled to −60° to −70°. A solution of 306 mg of methyl 4-(acetyloxy)-9-[[(1,1-dimethylethyl)dimethyl-silyl]oxy]16-methyl-11α-[(triethylsilyl)oxy]-16-[(trimethylsilyl)oxy]prosta-8,13E-dien-5-1-oate in 3 ml of diethyl ether was added, and the resulting mixture was stirred at −60° to −70° for five hours, then poured onto 0.5N hydrochloric acid solution, stirred, and extracted three times with diethyl ether. The combined organic phases were washed three times with saturated aqueous sodium chloride solution, three times with 5% sodium bicarbonate solution, and again with saturated sodium chloride solution, dried over sodium sulfate and filtered to give a colorless oil. The crude oil was purified by HPLC on silica gel using mixtures of methyl t-butyl ether and hexane to give a mixture of the following allenes

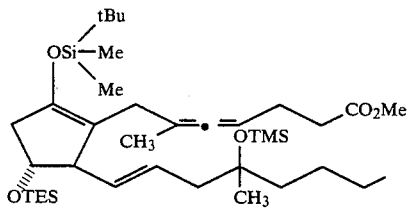

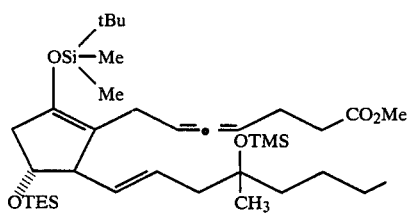

The mixture of above allenes was hydrolyzed in 3:1:1 acetic acid/tetrahydrofuran/water in two separate batches of 93 mg and 97 mg each. After stirring for 20 hours at room temperature, the reactions were combined for workup by pouring onto water and extracting three times with diethyl ether. The combined etheral layers were washed three times with saturated sodium chloride solution. The combined sodium chloride solutions were backwashed once with diethyl ether and this ether layer was combined with ether layers from the above extractions. The combined ether solutions were dried over sodium sulfate, filtered and stripped to give the crude product. The product was purified by HPLC on silica gel using mixtures of dioxane and isoctane to give the product methyl 11α, 16-dihydroxy-6,16-dimethyl-9-oxoprosta-4,5 13E-trien-1-oate containing a trace amount of impurity. As another product, there was also obtained methyl 11α, 16-dihydroxy-16-methyl-9-oxoprosta-4,5 13E-trien-1-oate.

The slightly impure title compound was dissolved in diethyl ether and washed three times with saturated sodium chloride solution. The combined aqueous layers were washed with diethyl ether and combined with the ether layers from the first washing. The combined ether layers were dried over sodium sulfate, filtered and stripped to give a crude oil. Chromatography of the crude material on silica gel using 60% ethyl acetate/hexane as the eluent gave the title compound having the following structure

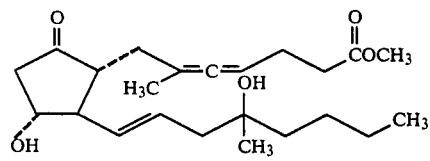

NMR: (CDCl₃, ppm): 5.05 (allene H); 1.15 (—CCH₃(OH)—); 4.10 (—CH(OH)—); 3.65 (OMe); 1.62 (d, Me on allene).

EXAMPLE 19

Preparation of methyl 8-[3α-hydroxy-2β-(4-hydroxy-4-methyl-1E-octenyl)-5-oxo-1α-cyclopentyl]-6-methyl-4,5 octadienoate Substitution of the appropriate starting material and substitution of the eluents dioxane and isooctane for the eluents methyl t-butyl ether and hexane called for in Example 18 afforded, by the procedure there detailed, the title product having the following structure

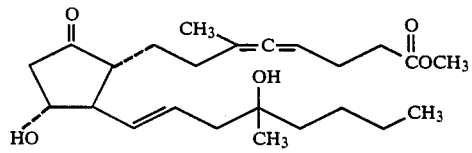

NMR: (CDCl₃, ppm) 1.62 (d, J=2–3 Hz, allene CH₃), 5.05 (allene H), 3.68 (OCH₃).

EXAMPLE 20

Preparation of ±methyl 8-[3α-hydroxy-2β-(4-hydroxy-4-methyl-1E-octenyl)-5-oxo-1α-cyclopentyl]-7-methyl-5,6-octadienoate Substitution of the appropriate starting material and substitution of the eluents dioxane and isooctane for the eluents methyl t-butyl ether and hexane called for in Example 18 afforded, by the procedure there detailed, the title product which was separated into the following two isomers

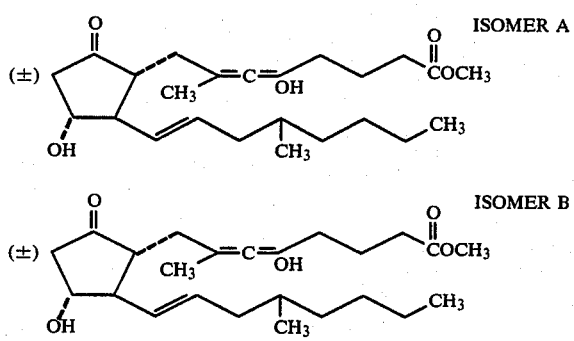

ISOMER A

ISOMER B

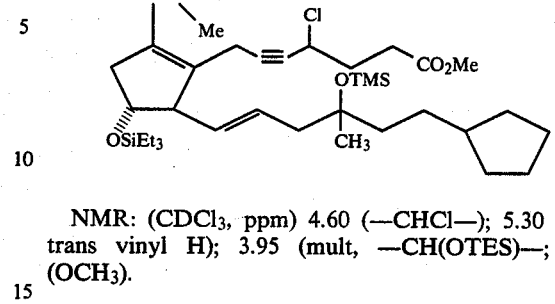

NMR: (CDCl₃, ppm) 4.60 (—CHCl—); 5.30 (mult trans vinyl H); 3.95 (mult, —CH(OTES)—; 3.68 (OCH₃).

EXAMPLE 23

Preparation of methyl 7-[5β-[6-cyclopentyl-4-methyl-4-[(trimethylsilyl)oxy]-1E-hexenyl]-2-[[(1,1-dimethylethyl)dimethylsilyl]oxy]-4α-[(triethylsilyl)oxy]-1-cyclopenten-1-yl]-4,5-heptadienoate The title compound was prepared by the method of Example 16 using 274 mg of methyl-4-chloro-7-[5β-[6-cyclopentyl-4-methyl-4-[(trimethylsilyl)oxy]-1E-hexenyl]-2-[[(1,1-dimethylethyl)dimethylsilyl]oxy]-4α-[(triethylsilyl)oxy]-1-cyclopenten-1-yl]-5-heptynoate 99 mg of zinc copper couple in 5 ml of ethanol and glacial acetic acid (50 mg). Chromatography of the crude material on a silica gel column using ethylacetate/hexane as the eluent afforded the title compound having the following structure

EXAMPLE 21

Preparation of methyl 7-[5β-[6-cyclopentyl-4-methyl-4-[(trimethylsilyl)oxy]-1E-hexenyl]-2-[[(1,1-dimethylethyl)dimethylsilyl]oxy]-4α-[(triethylsilyl)oxy]-1-cyclopenten-1-yl]-4-hydroxy-5-heptynoate The title compound was prepared according to the method of Example 1 using 998 mg of 3β-[6-cyclopentyl-4-methyl-4-[(trimethylsilyl)oxy]-1E-hexenyl]-1-[[(1,1-dimethylethyl)dimethylsily]oxy]-2-(propynyl)-4-[(triethylsily)oxy]cyclopentene, 1.1 ml of a solution of n-butyllithium in hexane (1.6M) and 378 mg of 3-formyl propanoate in tetrahydrofuran. Chromatography of the crude product on silica gel using 5% ethyl acetate/hexane as the eluent afforded the title compound having the following structure

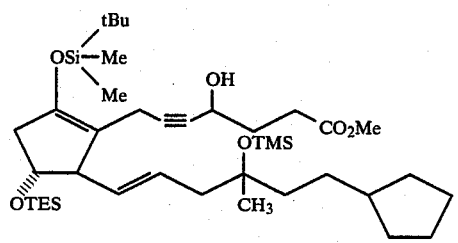

NMR: (CDCl₃, ppm) 5.30 (mult, trans vinyl H); 3.65 (OCH₃) 4.35 (—CH(OH)—); 3.95 (—CH(OTES)—).

EXAMPLE 22

Preparation of methyl 4-chloro-7-[5β-[6-cyclopentyl-4-methyl-4-[(trimethylsilyl)oxy]-1E-hexenyl]-2-[[(1,1-dimethylethyl)dimethylsilyl]oxy]-4α-[(triethylsilyi)oxy]-1-cyclopenten-1-yl]-5-heptynoate The title compound was prepared by the method of Example 15 using 353 mg of methyl 7-[5β-[6-cyclopentyl-4-methyl-4-[(trimethylsilyl)oxy]-1E-hexenyl]-2-[[(1,1-dimethylethyl)dimethylsilyl]oxy]-4α-[(triethylsilyl)oxy]-1-cyclopenten-1-yl]-4-hydroxy-5-heptynoate in 15 ml of diethyl ether, 369 mg of carbon tetrachloride and 238 mg of hexamethylphosphorous triamide. Chromatography of the crude material on a silica gel column using ethyl acetate/hexane as the eluent afforded the title compound having the following structure

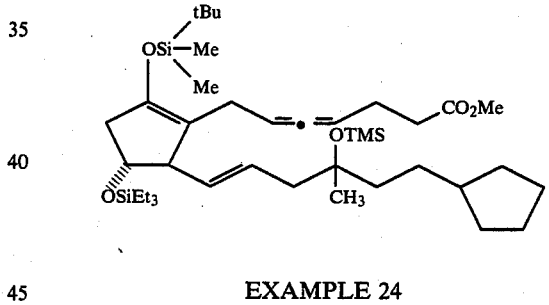

EXAMPLE 24

Preparation of methyl 7-[2β-[6-cyclopentyl-4-hydroxy-4-methyl-1E-hexenyl]-3α-hydroxy-5-oxo-1α-cyclopentyl]-4,5-heptadienoate The title compound was prepared by the method of Example 17 using 29 mg of methyl 7-[5β-[6-cyclopentyl-4-methyl-4-[(trimethylsilyl)oxy]-1E-hexenyl]-2-[[(1,1-dimethylethyl)dimethylsilyl]oxy]-4α-[(triethyslilyl)oxy]-1-cyclopenten-1-yl]-4,5-heptadienoate and 4 ml of a 3:/1:1 mixture of acetic acid/tetrahydrofuran/water. Chromatography of the crude material on a silica gel column using ethyl acetate/hexane as the eluent afforded the title compound having the following structure

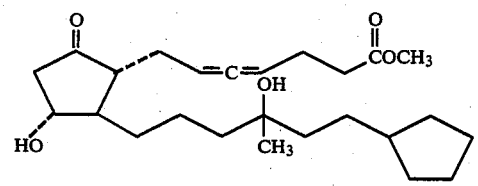

NMR (CDCl$_3$, ppm): 1.16 (s, —CCH$_3$(OH)—); 3.65 (OCH$_3$) 4.05 (mult, —CH(OH)—); 5.08 (mult allene H); 5.51 (mult, trans vinyl H C-13,4).

What is claimed is:

1. A compound of the formula

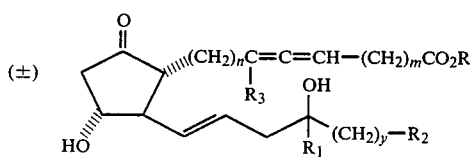

XIV wherein R is hydrogen; or straight or branched chain alkyl of 1 to 6 carbon atoms, inclusive
 wherein R$_1$ is hydrogen; or straight or branched chain alkyl of 1 to 6 carbon atoms, inclusive; or vinyl (—CH=CH$_2$)
 wherein R$_2$ is straight or branched chain alkyl of 1 to 6 carbon atoms; or cycloalkyl group containing 3 to 6 carbon atoms; or phenyl; or phenoxy
 wherein R$_3$ is hydrogen; or straight chain alkyl of 1 to 3 carbon atoms
 wherein m is an integer of from 1 to 4, inclusive;
 wherein n is an integer of from 1 to 3, inclusive with the proviso that the sum of m and n does not exceed 5;
wherein y is an integer of from 1 to 3;
± refers to the compound shown, its mirror image and the mixture of racemates.

2. A compound according to claim 1 wherein R$_3$ is hydrogen.

3. Methyl 11α, 16-dihydroxy-16-methyl-9-oxo-prosta-4,5,13E-trien-1-oate, a compound according to claim 2.

4. Methyl 8-[3α-hydroxy-2β-(4-hydroxy-4-methyl-1E-octenyl)-5-oxo-1α-cyclopentyl]-5,6-octadienoate, a compound according to claim 2.

5. Methyl 8-[3α-hydroxy-2β-(4-hydroxy-4-methyl-1E-octenyl)-5-oxo-1α-cyclopentyl]-4,5-octadienoate, a compound according to claim 2.

6. Methyl 11α,16-dihydroxy-16-methyl-9-oxoprosta-3,4,14E-trien-1-oate, a compound according to claim 2.

7. Methyl 7-2β-(6-cyclopentyl-4-hydroxy-4-methyl-1E-hexenyl)-3α-hydroxy-5-oxo-1α-cyclopentyl]-4,5-heptadienoate, a compound according to claim 2.

8. A compound according to claim 1 wherein R$_3$ is straight chain alkyl of 1 to 3 carbon atoms.

9. Methyl 8-[3α-hydroxy-2β-(4-hydroxy-4-methyl-1E-octenyl)-5-oxo-1α-cyclopentyl]-6-methyl-4,5-octadienoate, a compound according to claim 8.

10. (±) methyl 8-[3α-hydroxy-2β-(4-hydroxy-4-methyl-1E-octenyl)-5-oxo-1α-cyclopentyl]-7-methyl-5,6-octadienoate Isomer A, a compound according to claim 8.

11. (±) methyl 8-[3α-hydroxy-2β-(4-hydroxy-4-methyl-1E-octenyl)-5-oxo-1α-cyclopentyl]-7-methyl-5,6-octadienoate Isomer B, a compound according to claim 8.

12. Methyl 11α,16-dihydroxy-6,16-dimethyl-9-oxo-prosta-4,5,13E-trien-1-oate.

* * * * *